United States Patent [19]

Luft

[11] 3,968,370

[45] July 6, 1976

[54] NON-DISPERSIVE INFRARED GAS ANALYZER

[75] Inventor: Karl Friedrich Luft, Essen, Germany

[73] Assignee: Bergwerksverband GmbH, Essen, Germany

[22] Filed: Dec. 26, 1974

[21] Appl. No.: 536,332

[30] Foreign Application Priority Data

Jan. 3, 1974 Germany.............................. 2400221

[52] U.S. Cl................................. 250/344; 250/343
[51] Int. Cl.² ............................................ G01J 1/00
[58] Field of Search..................... 250/344, 343, 346

[56] References Cited
UNITED STATES PATENTS

| | | | |
|---|---|---|---|
| 2,924,713 | 2/1960 | Liston................................. | 250/344 |
| 3,005,097 | 10/1961 | Hummel............................. | 250/346 |
| 3,130,302 | 4/1964 | Liston et al........................ | 250/344 |
| 3,476,934 | 11/1969 | Luft.................................... | 250/344 |
| 3,517,189 | 6/1970 | Meyer................................. | 250/344 |

Primary Examiner—Alfred E. Smith
Assistant Examiner—B. C. Anderson
Attorney, Agent, or Firm—Malcolm W. Fraser

[57] ABSTRACT

An auxiliary signal for the compensation of the difference signal created in optical-pneumatic receivers due to the absorption of radiation, such compensation being achieved by one or more electrical-pneumatic transmitters connected directly to the receiver chambers.

8 Claims, 2 Drawing Figures

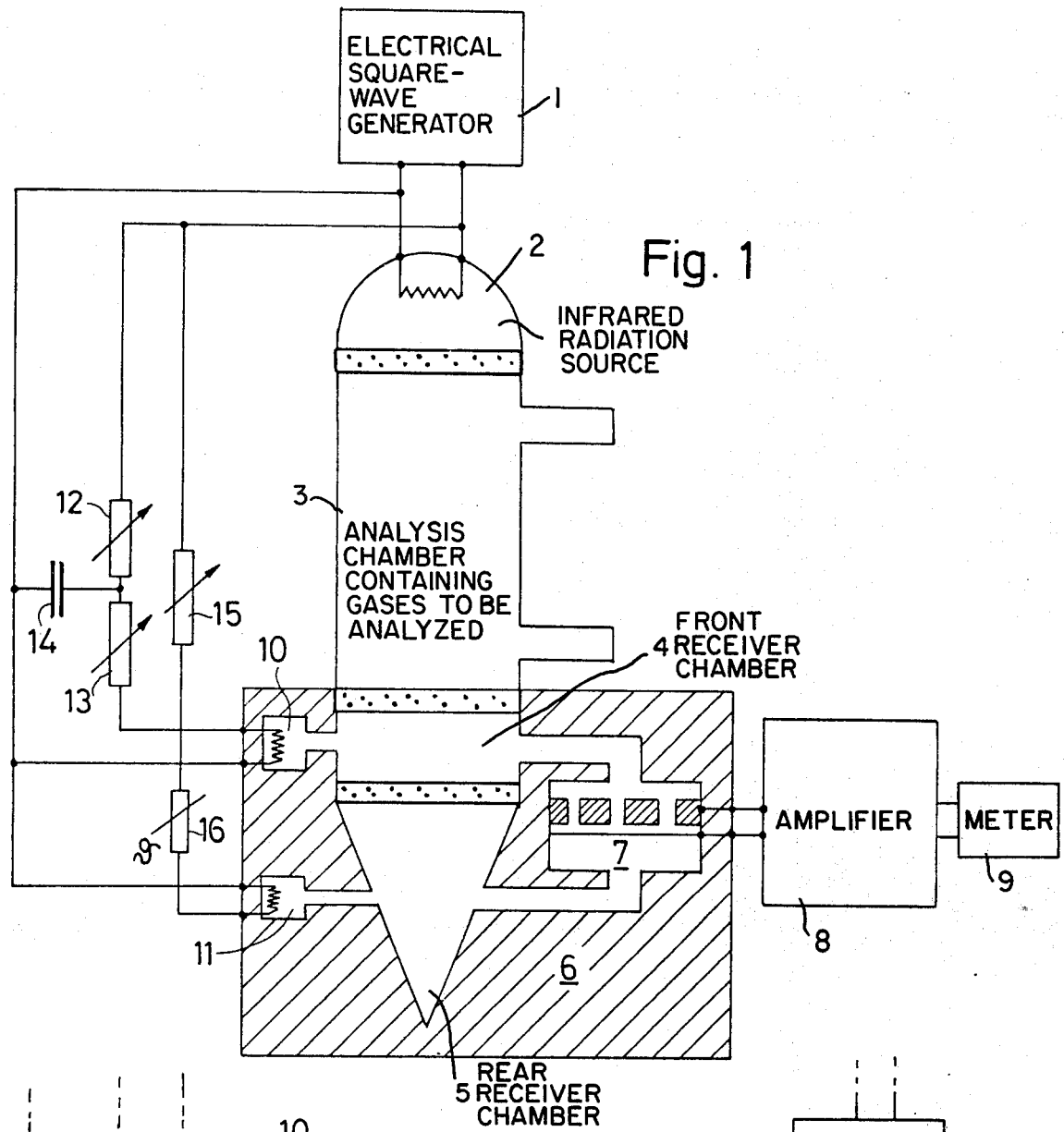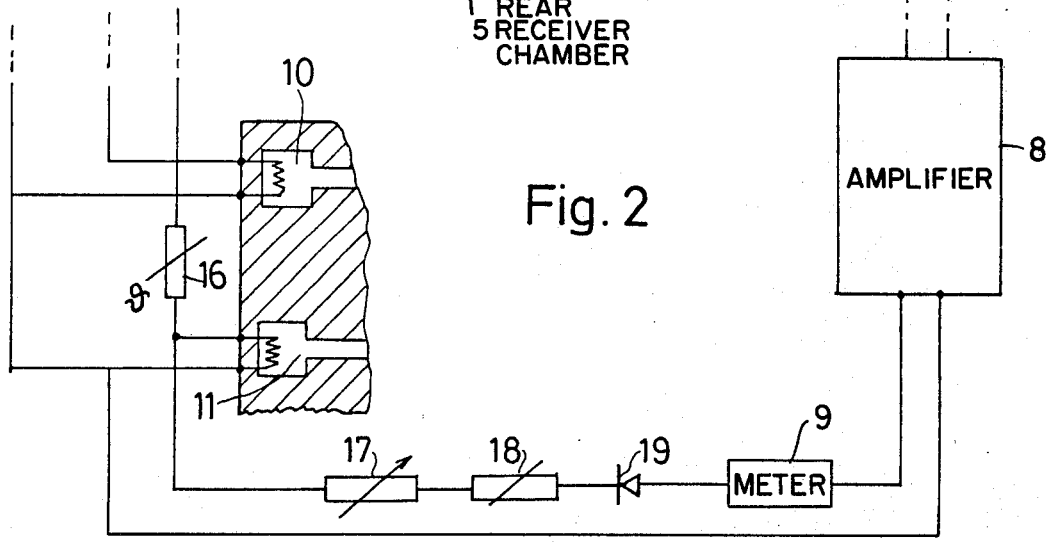

3,968,370

NON-DISPERSIVE INFRARED GAS ANALYZER

BACKGROUND OF THE INVENTION

The invention concerns a nondispersing infrared (IR) gas analysis device for the purpose of determining the concentration of a gas in a mixture of gases, where modulated IR radiation, after passing through the mixture of gases to be analyzed, arrives in a single-beam double-layer receiver with two receiver chambers filled with a selectively absorbing gas and arranged one after the other in the passage of the beam.

In devices of this type, the energy from the wavelength range which is most effectively absorbed by the receiver gas, for example, the energy from the center of an absorption line, makes up most of the energy absorbed in the front receiver chamber. As a result of the preliminary absorption in the front chamber, energy from less effective wavelengths, for example, the wavelengths located at the sides of an absorption line, makes up most of the energy absorbed in the rear, generally longer, receiver chamber. The difference in the radiation energies which are absorbed in the two receiver chambers, and the resulting difference in the thermal or pneumatic signals which are produced in the two chambers by this absorption, are indicative of the concentration of the gas which is to be measured in the mixture of gases. At the zero point of the measurement, that is, when the concentration of the gas which is to be measured is equal to zero, this difference in the signals is ideally equal to zero, meaning that the signals from the receiver chambers must have both the same amplitude as well as the same phase. These conditions cannot be fulfilled without difficulty in the case of a pure single beam arrangement in accordance with German Patent No. 1,017,385, corresponding to U.S. Pat. 2,951,939 of a source of radiation, an analysis cuvette, and the receiver, as a result of the different geometry and absorption distribution of the chambers. On the other hand, this device offers the advantage of simple construction and an optimal utilization of the radiation so that it is possible, by using it, to produce particularly small portable devices with a low consumption of electrical power.

For the purpose of solving the signal balance problem, it has already been suggested that the thermal time constants of the two chambers be adapted to each other by means of special designing of the shape of the rear receiver chamber, for example, see Russian Pat. No. 178,158. In accordance with another suggestion, the pneumatic balance is supposed to be achieved with the aid of supplementary capillaries and dead volumes, see German Patent (Auslegeschrift) No. 1,183,280 and similar U.S. Pat. No. 3,105,147. However, because of the unavoidable differences caused by manufacturing tolerances and the possible modification of the chambers from the outside over a period of time, these balance devices have to be adjustable without impairing the tightness of the vacuum, and thus these devices lead to considerable additional costs and increase the danger of the susceptibility of the devices to trouble.

In addition, in accordance with the German Patent (Auslegeschrift) No. 1,598,893 and similar U.S. Pat. No. 3,476,934, it was suggested that the signal transmitted by the receiver at the zero point of the measurement be compensated by means of an auxiliary signal with adjustable amplitude and phase. In doing this, the auxiliary signal is supposed to be produced with the aid of a second source of radiation modulated with the same frequency as the main source of radiation, or be supplied as an electrical signal to a different point in the measurement circuit formed by the receiver and amplifier.

The use of an auxiliary radiation source has the advantage that the compensation is accomplished at the start of the measurement circuit and that as a result of this, the auxiliary signal is subjected, to a large extent, to the same magnitudes of influence and disturbance as the main signal. However, this advantage must nevertheless be accepted along with higher costs for the mechanical-optical construction and for electrical power for the heating of the auxiliary source of radiation.

SUMMARY OF THE INVENTION

It is the goal of the present invention to produce the auxiliary signal for the compensation of the difference signal created in optical-pneumatic receivers due to the absorption of radiation in a particularly simple way with a low additional expense and with low, almost negligible, electrical power consumption and thereby to facilitate the construction of small portable IR gas analysis devices operating within the range of intrinsically safe electrical circuits, such as devices which are needed for operating and safety monitoring of the pit atmosphere in soft coal mining.

The nondispersing IR gas analyzer of the aforementioned type is characterized in accordance with the invention by the fact that the compensation of the difference signal is accomplished by means of one or more electrical-pneumatic transmitters which are connected directly to the receiver chambers.

This compensation can be accomplished even with a single pressure transmitter connected to one of the two receiver chambers, but it then nevertheless requires an electronic expense for the production and stabilization of the electrical control signal, which is not always desirable.

The compensation of the difference signal can be accomplished particularly simply and advantageously by means of using two pressure transmitters, one of which is connected to the front receiver chamber and is controlled through an adjustable electrical delay circuit, while the other is connected to the rear chamber and is controlled through an adjustable, preferably ohmic resistance by a modulation device which serves as a source of voltage and which is shared with the radiation source. It is expedient for a generator which produces a pulsing voltage with a preferably square-wave shape to be used as a voltage source.

Both the difference zero signal and the difference gas signal which occurs due to the presence of the gas component that is to be measured in the gas mixture can be compensated with the aid of the pressure transmitter. For this reason, in accordance with the invention, the difference signal transmitted from the receiver in one embodiment is supplied, after amplification, to one of the two pressure transmitters or to an additional pressure transmitter connected with one of the two receiver chambers, whereby means are supplied which are well known per se to adjust the amplitude and phase position of the returned signal in such a way that a pneumatic signal countercoupling occurs in the receiver which is sufficient for the stabilization of the signal.

It is appropriate, for good compensation, to make certain that the curve shape of the pneumatic auxiliary signal is as similar as possible to the receiver chamber signals occurring due to radiation absorption.

Although such an adaptation can also be achieved with the aid of electrical filters, it is more expedient and simple for the device in accordance with the invention to use pressure transmitters, above signal characteristic is adapted to that of the source of radiation, for example, thermal pressure transmitters while using electrically pulsed thermal sources of radiation.

For this reason, it is advantageous to use electrically pulsed hot wire transmitters for the production of the auxiliary signals in the case of the electrically pulsed thermal sources of radiation which come into consideration in particular at present for use in IR gas analysis devices of the aforementioned type.

In the case of producing the modulated radiation by other means, such as, for example, with the aid of pulsed lasers or laser diodes or by means of rotating shutters, it will be advantageous in some circumstances to use other pressure transmitters such as, for example piezoelectric transmitters, which are not affected by thermal inertia.

The arrangement, in accordance with the invention, can be expanded in a simple way so that errors caused by environmental influences are excluded. In accordance with the invention, this zero point and reading error caused by variations in temperature and pressure can be eliminated by installing temperature-dependent and pressure-dependent resistances in the control circuits of the pressure transmitter.

In the same way, the dependence of the measurement signal on the pressure and temperature of the gas mixture being analyzed can be eliminated by installation of pressure-dependent and temperature-dependent resistances in the countercoupling circuit.

BRIEF DESCRIPTION OF THE DRAWING

The embodiment of the invention operating with electrically pulsed thermal sources or radiation and thermal pressure transmitters will be explained in greater detail in the following.

FIG. 1 illustrates a two-layer receiver.

FIG. 2 illustrates an alternate form of two layer receiver.

DESCRIPTIONS OF THE PREFERRED EMBODIMENTS

With the aid of a rectangular (i.e., square-wave) voltage supplied by the generator 1, the radiation source 2 consisting of a thin hot conductor strip is heated periodically with a frequency of a few Hz. One portion of the modulated IR radiation which is transmitted by the radiation source 2 arrives, after passing through the cuvette (i.e., analysis chamber) 3 containing the mixture of gases that is to be analyzed, into the chambers 4 and 5 of the two-layer reveiver 6 which are located one after the other in the path of the beam, and the radiation produces pressure impulses there in a well known way due to radiation absorption in the receiver gas. The difference in the pressure impulses in the two chambers is measured by the diaphragm capactor 7 to provide an electrical difference signal which is fed to an amplifier 8 and then to a measurement instrument 9.

Since the preliminary absorption in the cuvette 3 weakens essentially only the signal of the front chamber 4, the measurement signal which is produced at this time has a direction which is practically opposite to this chamber signal. On the other hand, the difference zero signal — which is produced due to the incomplete amplitude and phase balance of the receiver chamber signals and which occurs in the zero point of the measurement, that is, without preliminary absorption in cuvette 3 — can have a completely different direction and amplitude depending upon the magnitude of the differences in amplitude and phase. Nevertheless, it can always be split up into two components, one of which runs in the direction of the measurement signal and which is added to or subtracted from it, and the other of which is rotated by 90° with respect to the measurement signal.

In the case of the exemplified embodiment taken as a basis for FIG. 1, it is also assumed that at the zero point, the signal produced due to radiation absorption in the rear receiver chamber 5 has a lower amplitude than the signal from the front chamber 4 and has a lag phase as a result of the higher thermal time constant in the generally longer chamber 5. These are assumptions which do not constitute any limitation of the field of application of the concept of the invention.

The compensation device in accordance with the invention which is shown in FIG. 1 adapts itself completely to this factual situation. It consists of the heating coils 10 and 11 which are installed in auxiliary chambers connected to the receiver chambers to act as pneumatic pressure transmitters (i.e., pressure generators). The radiation source voltage, applied through a delay circuit consisting of the resistances 12 and 13 and the capacitor 14, provides a control signal which controls the heating filament 10 in such a way that an auxiliary signal which lags by about 90° is superimposed on the signal in the receiver chamber 4, and the amplitude of the auxiliary signal has dimensions which are such that it compensates for the 90° component of the difference zero signal occurring due to the lagging of the signal of the rear chamber 5. The remaining signal, which is in phase with the measurement direction and which is caused by the difference in amplitude of the chamber signals, is compensated for with the aid of the second auxiliary signal transmitted to the chamber 5 by the heating filament 11, whereupon the control is accomplished without a delay device by a control signal passed through the resistances 15 and 16.

It is assumed when this is done that the phases of unretarded auxiliary signals correspond to a great extent with those of the chamber signals occurring due to radiation absorption. This condition can be achieved without particular difficulties by means of using appropriate dimensions for the heating wires. Nevertheless, if phase differences still occur, for example, as can be the case when using pressure transmitters that are particularly easy to manufacture in the form of the filaments of small incandescent bulbs, then these differences can be compensated for easily with the aid of additional resistor-capacitor (RC) elements in the control lines of the transmitter or even of the radiation source. For example, if the time constant of the heating process caused by such a filament is lower than in the case of radiation absorption, an RC element is also installed in the control circuit of the heating filament 11 so that the phases can be made to correspond by means of the retardation of the auxiliary signal which is accomplished in this way.

In the place of inactive RC circuits, active electronic switching circuits can also be used in a way which is well known per se for the purpose of producing the phase-shifted auxiliary signals. As a result of their better flexibility, not only differences in the phases but also differences in the curve shape of the chamber signals can be compensated for with their aid, whereby any harmonics of the difference zero signal which may be present are eliminated.

A further form of embodiment of the invention is shown in FIG. 2. As before, the signal transmitted by the heating filament 10 serves to compensate for the 90° component of the difference zero signal, while that from the filament 11 compensates for the difference in amplitude of the receiver chamber signals.

Nevertheless, if a difference measurement signal occurs due to preliminary absorption in the cuvette 3, then this signal is amplified in the amplifier 8 and is likewise supplied as a control signal to the heating filament 11 through the resistances 17 and 18 and the diode 19. When this is done, the preliminary resistances 15 and 16 or 17 and 18 are high with respect to the resistance of the heating filament, so that voltages which are supplied by the voltage source of the radiation source or by the amplifier are added vectorially relatively independently of each other. It goes without saying that an additional pressure transmitter supplied with the measurement signal can also be used for the purpose of complete separation of the two control voltages.

If, by means of amplifier-engineering measures and poling of the diode 19, one arranges things in such a way that the phase of the auxiliary signals (produced by the heating filament 11 or by an additional heating element connected with chamber 5 by means of the measurement signal) is shifted by 180° with respect to the difference measurement signal in the receiver, then the measurement circuit consisting of the diaphragm compensator and amplifier will be stabilized to a large extent by the negative feedback which therefore exists and which can be adjusted with the aid of the series resistances 17 and 18.

When this is done, the electrical power which is determined with the aid of voltage or current measurement and which is supplied to the heating filament is an indication of the concentration of the gas components which is to be measured. The resistances 16 and 18 are temperature-dependent or pressure-dependent resistances and serve to eliminate the influences of the temperature on the zero point or of the influences of temperature and pressure on the measurement signal.

Other measurement engineering tasks, such as, for example, zero point suppression and functional testing by means of measurement value simulation can also be solved in a simple way by using the device in accordance with the invention by an appropriate modification of the series resistances.

In addition to this advantage of the capacity for adaptation, there is primarily also the advantage of the negligibly low additional power requirement when thermal pressure transmitters are used. This is due to the smallness of the difference signals occurring in the receivers, due to radiation absorption, which are of the order of magnitude of $10^{-3}°C$ or $10^{-2}mmWs$. Thus, an electrical power on the order of magnitude of only $10^{-4}$ Watts is needed for the control of a thermal pressure transmitter.

The problem stated at the outset of the construction of small and intrinsically safe IR gas analyzers can be solved in a particularly simple and appropriate way with the aid of the invention.

Above and beyond this, nondispersing IR analysis will prove to be useful in other areas of application as well.

What I claim is:

1. In a non-dispersing infrared gas analyzer comprising:
   a. a two-layer receiver including two receiver chambers,
   b. means for passing a single infrared beam having a given frequency, phase and amplitude through a test sample of gas into the two-layer receiver to produce a pressure difference in the two chambers,
   c. a modulated source of voltage for operating the single infrared beam, and
   d. means for generating an electrical difference signal substantially proportional to the pressure difference,
   the improved means to compensate the difference signal comprising:
   e. at least one electrically operated pneumatic pressure generator situated in one of the two receiver chambers for producing an auxiliary pressure signal, and
   f. means for producing an electrical control signal with a phase and frequency controlled by the phase and frequency of modulated source of voltage for electrically operating the pressure generator.

2. A device in accordance with claim 1, wherein said at least one electrically operated pneumatic pressure generator comprises two such generators, each operated by a control signal, and further comprising:
   a. means for pneumatically connecting a first of the two generators with a front one of the two receiver chambers,
   b. an adjustable electrical delay circuit responsive to the modulated source of voltage for providing a first control signal for electrically operating the first generator,
   c. means for pneumatically connecting a second of the two generators with a rear one of the two receiver chambers, and
   d. an adjustable resistance means for providing a second control signal, the adjustable signal being adjustable in amplitude while maintaining the same frequency as the infrared beam, and for applying the second control signal to operate the pressure generator.

3. A device according to claim 2, further comprising:
   a. means for amplifying the electrical difference signal,
   b. means for adjusting the amplitude and phase position of the amplified difference signal to provide a feedback signal,
   c. means for using the feedback signal to operate an electrically operated pneumatic pressure generator in one of the two receiver chambers.

4. A device according to claim 3, wherein the generator operated by the feedback signal is one of said two generators, the feedback signal being one of two signals applied to the generator in order to electrically operate it.

5. A device according to claim 3, wherein the signal characteristic of the pressure generators are adapted to that of the radiation source.

6. A device according to claim 5 wherein the modulated source of voltage operates an electrically pulsed thermal radiation source and the generators are pulsed thermal pressure generators such as hot-wire generators.

7. A device according to claim 6 wherein temperature-dependent and pressure-dependent resistances are used in control circuits to eliminate errors in zero point caused by variations in temperature and pressure.

8. A device according to claim 6 wherein temperature-dependent and pressure-dependent resistances are used in a feedback circuit to eliminate dependency of the measurement signal upon pressure and temperature of the mixture of gasses.

* * * * *